US012616547B2

(12) United States Patent | (10) Patent No.: US 12,616,547 B2
Mirbahaeddin et al. | (45) Date of Patent: May 5, 2026

(54) PROTECTIVE SHIELD SYSTEM

(71) Applicant: SANAH I PRODUCTS, LLC, Carrollton, TX (US)

(72) Inventors: Majid Mirbahaeddin, Carrollton, TX (US); Eric Eiselt, Carrollton, TX (US)

(73) Assignee: Sanah I Products, LLC, Carrollton, TX (US)

( * ) Notice: Subject to any disclaimer, the term of this patent is extended or adjusted under 35 U.S.C. 154(b) by 223 days.

(21) Appl. No.: 18/358,880

(22) Filed: Jul. 25, 2023

(65) Prior Publication Data

US 2024/0033031 A1 Feb. 1, 2024

Related U.S. Application Data

(60) Provisional application No. 63/369,594, filed on Jul. 27, 2022.

(51) Int. Cl.
| | |
|---|---|
| *A61B 90/40* | (2016.01) |
| *A61B 90/00* | (2016.01) |
| *A61B 90/50* | (2016.01) |
| *A61C 17/06* | (2006.01) |

(52) U.S. Cl.
CPC .............. *A61B 90/05* (2016.02); *A61B 90/50* (2016.02); *A61C 17/06* (2019.05)

(58) Field of Classification Search
CPC ... A61B 90/50; A61B 90/40; A61B 2090/401; A61G 15/14; A61G 15/10; A61G 13/108; A61G 10/00; A61G 10/005; A61G 15/00; A61C 17/0208; A61C 19/007; A61C 17/06; A61M 16/009; A41D 13/11; A41D 13/1184; A41D 13/1161; A41D 13/1192; A41D 13/0025; A41D 13/1153; A62B 7/12; A62B 18/02; A62B 18/025; A62B 18/003; A62B 18/006; A61F 9/068; A61F 9/06; A61F 9/045; A61F 9/04
See application file for complete search history.

*Primary Examiner* — Victoria Hicks Fisher
(74) *Attorney, Agent, or Firm* — Perkins Coie LLP; Babak Tehranchi

(57) ABSTRACT

Methods, apparatus, and systems for reducing transmission of aerosol droplets in a medical or dental procedure are described. In one example aspect, a protective shield system comprises a base plate with a first cover and a second cover. The first cover and the second cover are configured to form at least part of a pipe system when coupled together. The pipe system includes two ducts and an interface configured to be connected to a vacuum suction system. The protective shield system includes two suction tubes removably coupled to the two ducts of the pipe system and a shield having at least one transparent section. The shield configured to be removably coupled to the base plate so as to allow attachment of the shield to the base plate prior to the medical or dental procedure and removal of the shield from the base plate after the medical or dental procedure.

10 Claims, 19 Drawing Sheets

100

107

105

101

103

300

319

315

319

320

400

500

500

1100

18.0″

6.0″

14″

1115    1103

1200

1210

ATTACH A SHIELD OF THE PROTECTIVE SHIELD SYSTEM TO A BASE PLATE OF THE PROTECTIVE SHIELD SYSTEM

1220

ADJUST A POSITION OR AN ORIENTATION OF THE BASE PLATE OF THE PROTECTIVE SHIELD SYSTEM

1230

CONNECT A PIPE OF THE PROTECTIVE SHIELD SYSTEM TO A SUCTION SYSTEM

1240

DETACH THE SHIELD FROM THE BASE PLATE AFTER THE COMPLETION OF THE MEDICAL OR DENTAL PROCEDURE

PROTECTIVE SHIELD SYSTEM

CROSS-REFERENCE TO RELATED APPLICATION(S)

This application claims the benefit of priority to U.S. Patent Application No. 63/369,594, filed on Jul. 27, 2022. The entire contents of the above-noted provisional application are incorporated by reference as part of the disclosure of this document.

BACKGROUND

A communicable disease is one that is spread from one person to another through a variety of ways, such as contact with blood and bodily fluids or breathing in an airborne virus. From the coronavirus-caused COVID-19 to influenza, Lyme disease malaria and Ebola, outbreaks of infectious diseases can have an extraordinary impact on human health. Preventing and controlling the spread of disease is at the heart of much public health work.

DETAILED DESCRIPTION

Communicable diseases pose risks to societies in a variety of ways. The recent COVID-19 pandemic has brought big challenges to communities and healthcare professionals. In response to the recent COVID-19 pandemic in the United States, Centers for Disease Control and Prevention (CDC) recognizes the need to provide necessary healthcare services while minimizing risk to patients and healthcare personnel. CDC has developed a framework for healthcare personnel and healthcare systems for delivery of care during the pandemic, such as the use of personal protection equipment (PPE). Similarly, guidelines have been issued for dental health care, which is also an integral part of the public health framework. Health and dental care professionals should wear a surgical mask, eye protection, and a gown or protective clothing during procedures likely to generate splashing or spattering of blood or other body fluids. Healthcare facilities must ensure that any reusable PPE is properly cleaned, decontaminated, and maintained after and between uses.

While the use of PPE increases the level of protection for healthcare professionals, it alone may not provide optimal protection. For example, performing aerosol-generating procedures on patients requires a higher level of protection for healthcare professionals. Currently, the CDC recommends the use of N95 respirators or other disposable filtering facepiece respirators, if available. However, such respirators should be used in the context of a respiratory protection program, which includes medical evaluations, training, and fit testing. Should a respirator become loose during or between procedures, a healthcare professional can be exposed to the virus and/or the risk of spreading the disease to subsequent patients is increased.

This patent document discloses techniques that can be implemented as a protective shield system to provide an increased level of protection for healthcare professionals in aerosol-generating procedures and situations that protection from airborne viruses, particulate and like are needed. Unlike N95 respirators or other disposable filtering face-piece respirators, the disclosed protective shield system does not require additional training or fit testing. Components of the protective shield system can be easily replaced or sanitized between procedures to minimize and/or eliminate the risk of transmitting communicable diseases from patients to healthcare professionals, from healthcare professionals to subsequent patients, and from patients to patients.

Figure 1A:
FIG. 1A illustrates an example configuration of a protective shield system used in a medical or dental procedure in accordance with one or more embodiments of the present technology.

FIG. 1A illustrates an example configuration of a protective shield system 100 used in a medical or dental procedure in accordance with one or more embodiments of the present technology. The protective shield system 100 includes a base plate 101 that is coupled to a ceiling via an adjustable arm 107. In some embodiments, the protective shield system 100 includes a handle 103 that is coupled to the base plate 101 to allow easy maneuver of the protective shield system 100. A healthcare professional can adjust the position and/or orientation of the base plate 101 using the handle 103 prior to or during the procedure to ensure that there is sufficient room to operate on the patient underneath the protective shield.

The protective shield system 100 also includes a transparent shield 105 that is removably coupled to the base plate 101. That is, the transparent shield can be placed onto the base plate as will be described herein, and can further be removed for cleaning, sterilization or disposal. During the procedure, the transparent shield 105 prevents aerosol droplets, mists and/or other particulates from passing to the healthcare professional, and from the healthcare professional to the patient. After the procedure is completed, the transparent shield 105 can be removed from the base plate 101 so that it is either replaced (e.g., disposable shield) or sanitized (e.g., reusable shield) for subsequent procedures. In some embodiments, an air pathway or a pipe system (not shown in FIG. 1A) is at least partially positioned within the base plate 101, and is connected to a vacuum suction system so that droplets or mist generated during the procedure can be drawn away from under the protective shield.

Figure 1B:
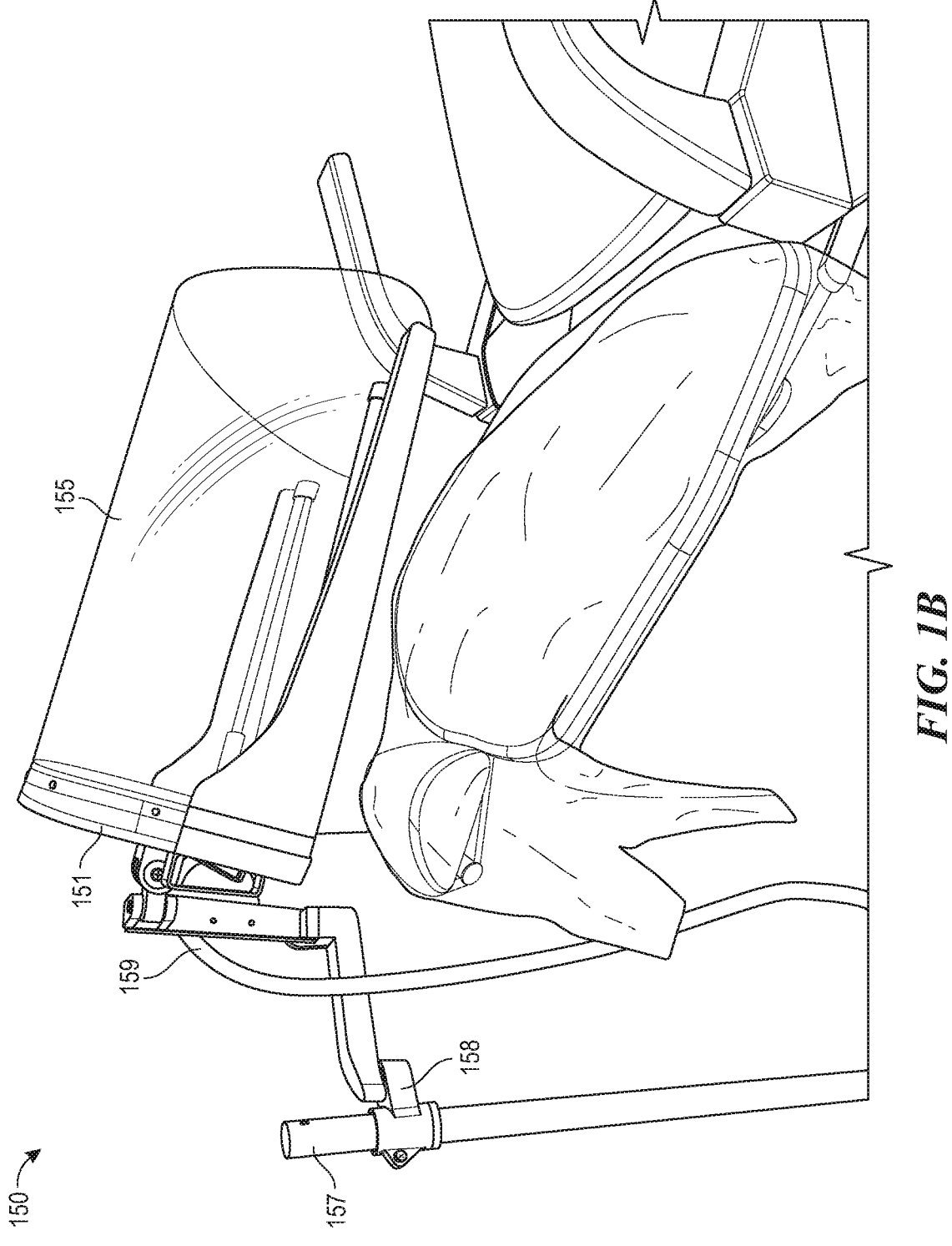
FIG. 1B illustrates another example configuration of a protective shield system used in a medical or dental procedure in accordance with one or more embodiments of the present technology.

FIG. 1B illustrates another example configuration of a protective shield system 150 that can be used in a medical or dental procedure in accordance with one or more embodiments of the present technology. The protective shield system 150 includes a transparent shield 155 that is removably coupled to a base plate 151. During the procedure, the transparent shield 155 prevents aerosol droplets, mists and/or other particulates from passing to the healthcare professional and from the healthcare professional to the patient. After the procedure is completed, the transparent shield 155 can be removed from the base plate 151 so that it is either replaced or sanitized for subsequent procedures.

In this example configuration of FIG. 1B, the base plate 151 is coupled to a portable platform 157. The portable platform 157 can include wheels (not shown) to allow positioning the portable platform at a desired location close to the chair. The portable platform 157 can include a bracket or holder 158 (e.g., an L-shaped bracket or holder as shown) to allow a vacuum hose 159 from a vacuum suction system to be coupled to a pipe system or an air pathway (not shown) that is at least partially positioned within the base plate 101. The portable platform 157 offers the protective shield system 150 greater mobility across different procedures and/or in operation rooms, with proper sanitization in between. In some configurations, the position of the bracket or holder 158 can be vertically adjusted. In some configurations, the bracket or holder 158 includes two sections forming an angle with respect to each other, and one or both of the sections can move to change the angle therebetween (e.g., from 30 degrees to 180 degrees).

Figure 2A:
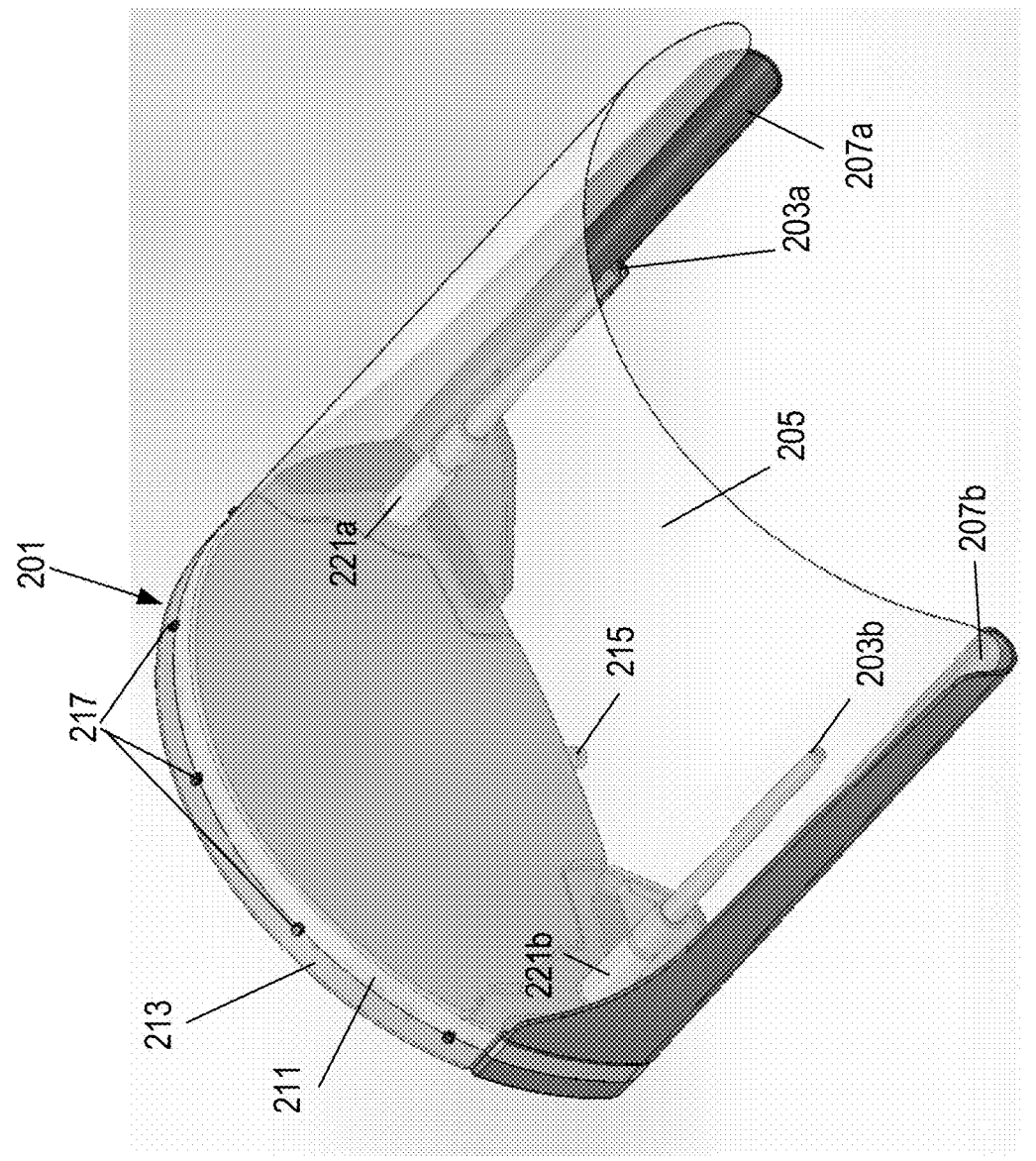
FIG. 2A illustrates a perspective view of an example protective shield system in accordance with one or more embodiments of the present technology.
Figure 2B:
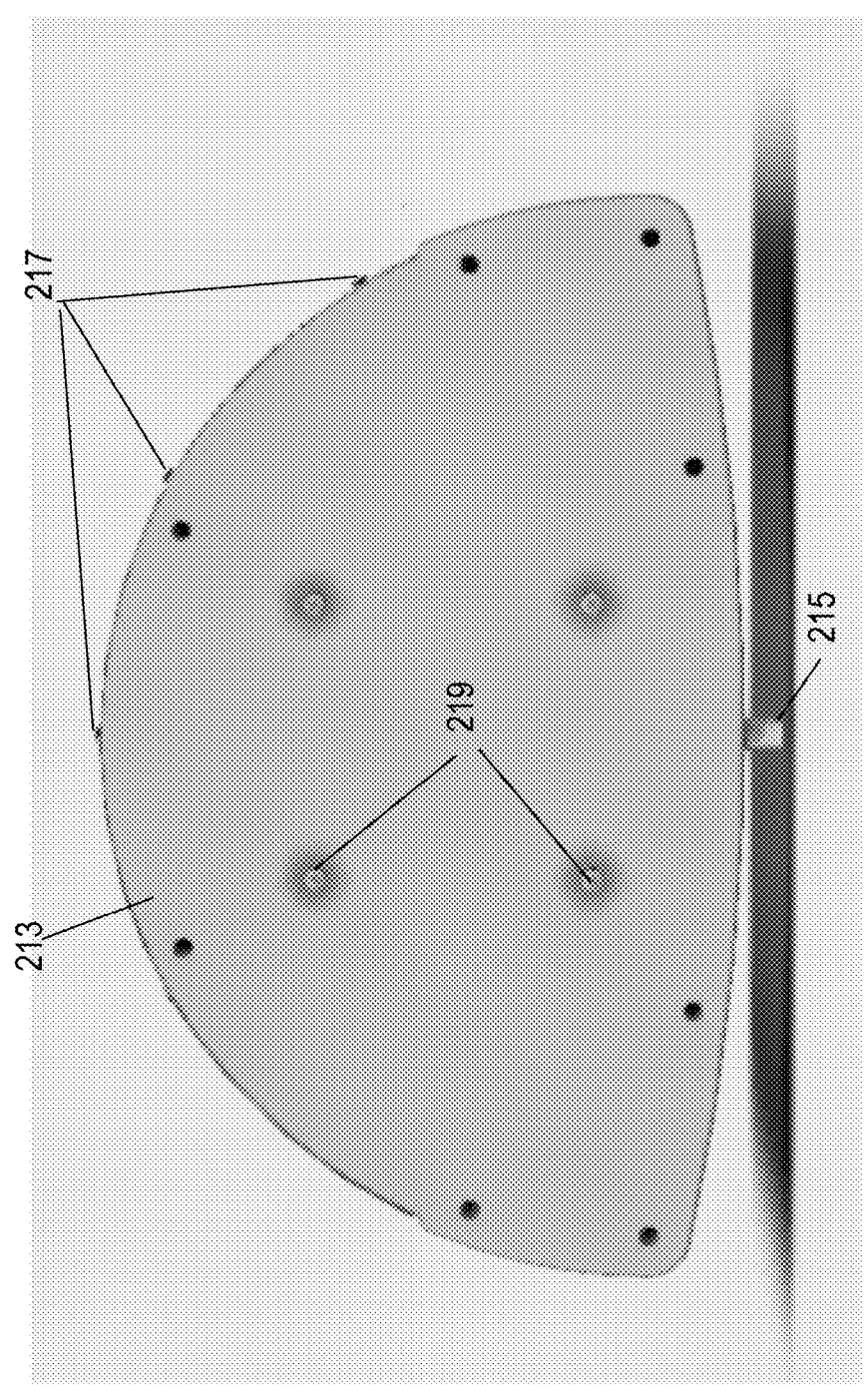
FIG. 2B illustrates a back view of the example protective shield system in FIG. 2A in accordance with one or more embodiments of the present technology.

FIGS. 2A-B illustrates an example protective shield system 200 in accordance with one or more embodiments of the present technology. FIG. 2A illustrates a perspective view of the example protective shield system 200. The protective shield system 200 includes a base plate 201, a transparent shield 205 that is removably coupled to the base plate 201, two suction modules 203a, 203b coupled to the base plate, and two fluid (or moisture) collection troughs 207a, 207b configured to collect fluids from the transparent shield 205 and also to facilitate airflow control. FIG. 2B illustrates a back view of the example protective shield system 200. The base plate 201 has a substantially flat back surface and has a curved edge. As illustrated in FIG. 2A, in some embodiments, the base plate includes two sections, e.g., a first section and a second section 213 can be coupled together using a coupling mechanism 219, such as one or more screws or nails.

Referring back to FIG. 2A, the base plate 201 can be made of a smooth solid material (e.g., hard plastic) so that it can be easily sanitized (e.g., by spraying or by wiping) between procedures. In some embodiments, the base plate 201 includes a first section 211 (e.g., a front cover) and a second section 213 (e.g., a back cover). The first section 211 and the second section 213, when coupled together, form at least part of a pipe system or air pathway that can be connected to a vacuum suction system (see, e.g., FIGS. 3A and 3B). Such design provides aesthetic appeal by enclosing the pipe system or air pathway within the closed chamber formed by the covers, thereby removing the need of having exposed tubing in the protective shield system. Additionally, or alternatively, in some embodiments, the use of some of all of the hoses or extraneous pipes within the base plate can be eliminated by providing conduits that are part of the base plate.

The pipe system can include an interface 215 and two ducts 221a, 221b. The interface 215 can be removably connected to the vacuum suction system. Two suction modules 203a, 203b can be removably coupled to/assembled with the two ducts 221a, 221b to draw aerosol droplets or mists and the like. In some embodiments, the suction modules are disposable and can be replaced between procedures. In some embodiments, the suction modules can be removed and sanitized at the end of the procedures. In some embodiments, the first section 211 and the second section 213, when coupled together, also form multiple shield retainers 217 that allow the transparent shield 205 to be removably and stably coupled to the base plate 201.

Figure 3A:
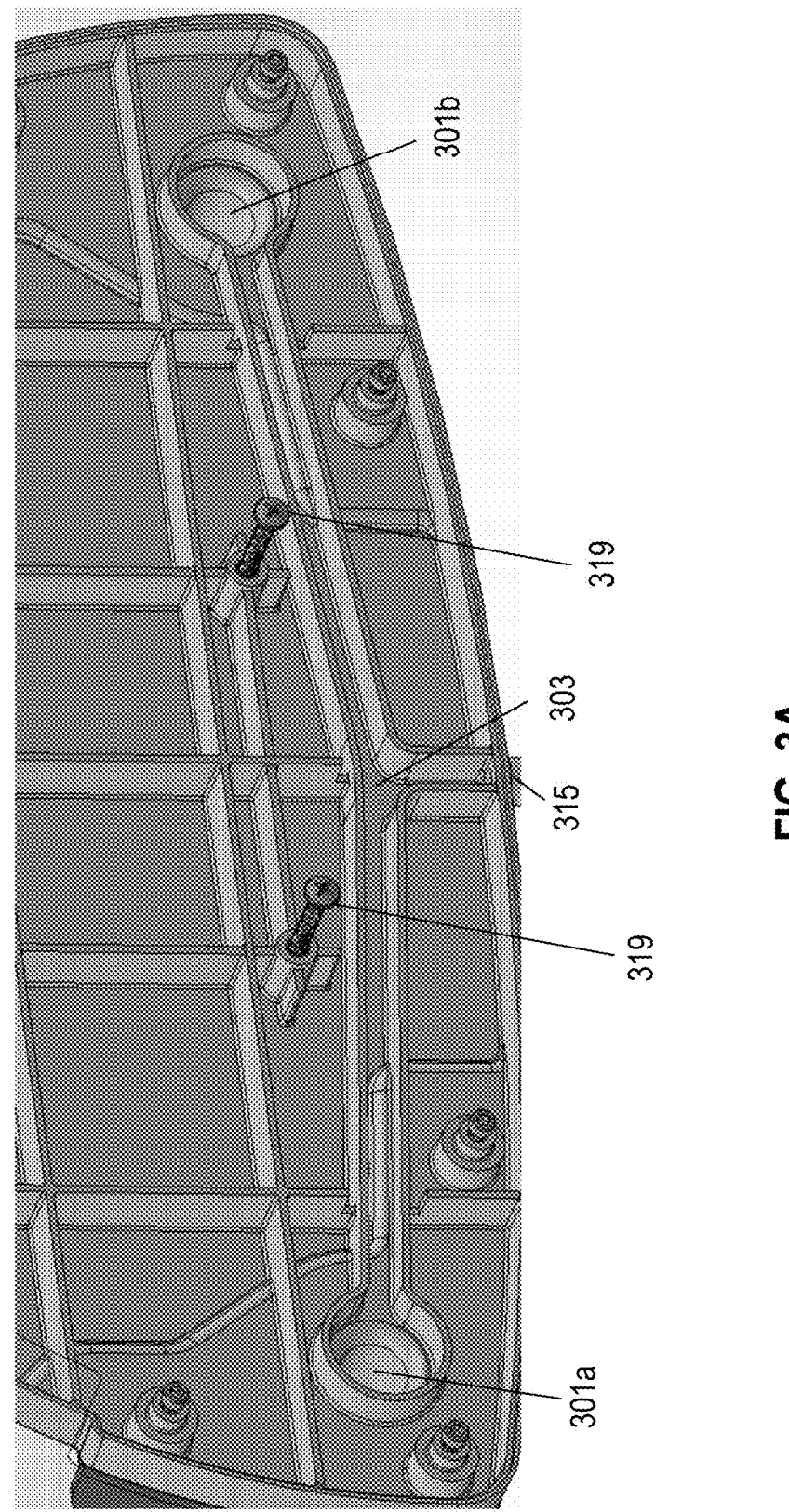
FIG. 3A illustrates an example second cover of an example protective shield system in accordance with one or more embodiments of the present technology.
Figure 3B:
FIG. 3B illustrates an example second cover of an example protective shield system with a sealing component in accordance with one or more embodiments of the present technology.

FIG. 3A illustrates an example of a first (or front) section 300 of a base plate of an example protective shield system in accordance with one or more embodiments of the present technology. In this example, a second (or back) base plate section (not shown) can be attached or detached from the first section 300 using the coupling mechanism 319 (e.g., one or more screws). In some embodiments, the one or both of the first or second base plate sections are structured to form at least part of a pipe system or air pathway that can be connected to an external vacuum suction system. FIG. 3A illustrates an example of such a first section 300 that includes end of two ducts 301*a*, 301*b* that extend outward from the front face of the first base plate section to be coupled to the suction modules. The first base plate section also includes a T-shaped channel 303 that connects the two ducts 301*a*, 301*b*. The bottom of the T-shaped channel 303 can form the interface 315 to allow a connection port for the vacuum suction system. FIG. 3B illustrates an example first section 300 with a seal 320 in accordance with one or more embodiments of the present technology. The seal 320 is shaped to cover and seal the two ducts 301*a*, 301*b* and the T-shaped channel 303 to prevent fluid (e.g., drawn by the pipe system) from leaking within the base plate. In some embodiments, the seal 320 can be a rubber seal or a silicone seal.

Figure 4A:
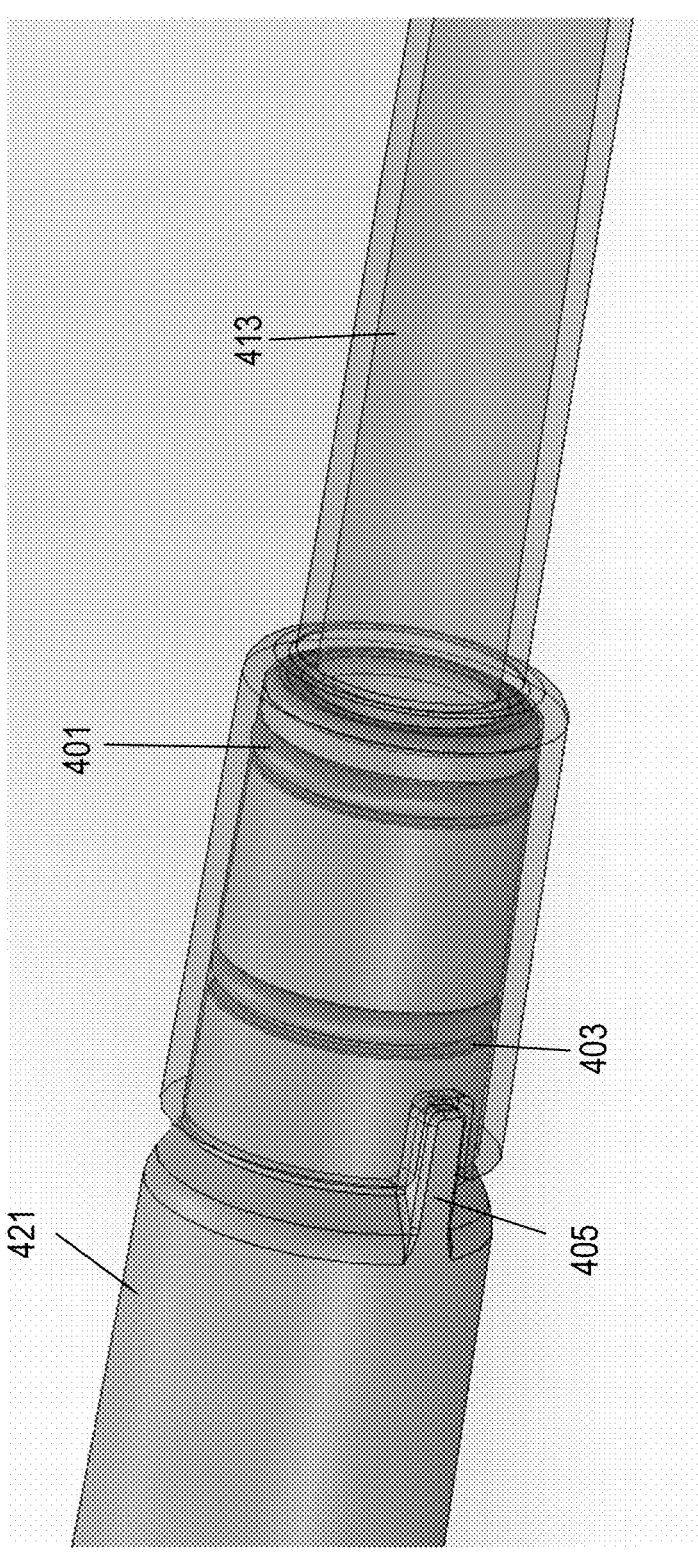
FIG. 4A illustrates a perspective view of an example coupling mechanism that can be used to enable the removable coupling of a suction tube with a duct in accordance with one or more embodiments of the present technology.
Figure 4B:
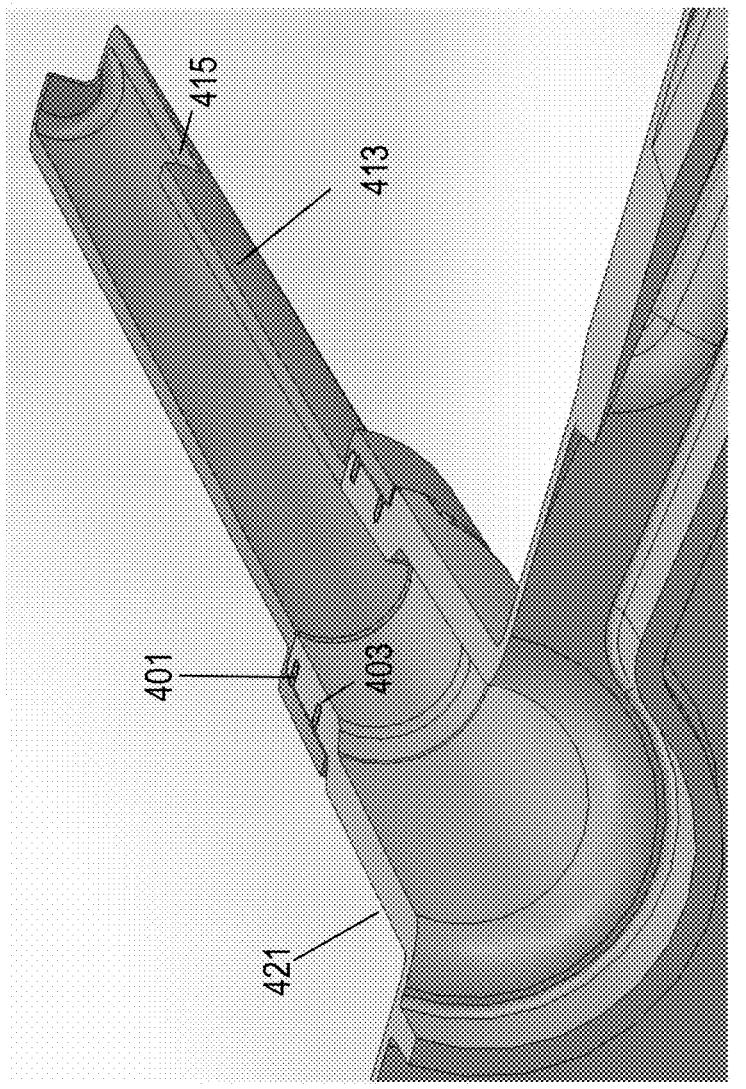
FIG. 4B illustrates a cross-section view of an example of a coupling mechanism that can be used to enable the removable coupling of a suction tube with a duct in accordance with one or more embodiments of the present technology.

Turning back to FIG. 2A, two suction modules 203*a*, 203*b* can be removably coupled to the two ducts 221*a*, 221*b* that is formed as part of the pipe system by the two covers of the base plate 201. FIGS. 4A-4B illustrate an example coupling mechanism 400 that can be used to enable the removable coupling of a suction module with a duct in accordance with one or more embodiments of the present technology. As shown in FIG. 4B, which illustrates a cross-section view of the coupling mechanism 400, one or more O-rings 401 (also known as a packing or a toric joint) can be positioned in one or more grooves 403. The one or more O-rings 401 are compressed during assembly of the duct 421 and the suction module 413, forming a airtight seal at the interface to prevent leaking of the droplets or fluid. FIG. 4A illustrates a perspective view of the example coupling mechanism 400. In some embodiments, as shown in FIG. 4A, the duct 421 can further include a ridge 405 to ensure that the suction module 413 is assembled at the desired direction. For instance, in the example configuration of FIGS. 4A and 4B, the ridge 405 engages with a corresponding opening or notch of the suction module 413 to allow the slit 415 (shown in FIG. 4B) to be oriented in a horizontal position (in the direction of the patient) during the procedure.

Figure 5A:
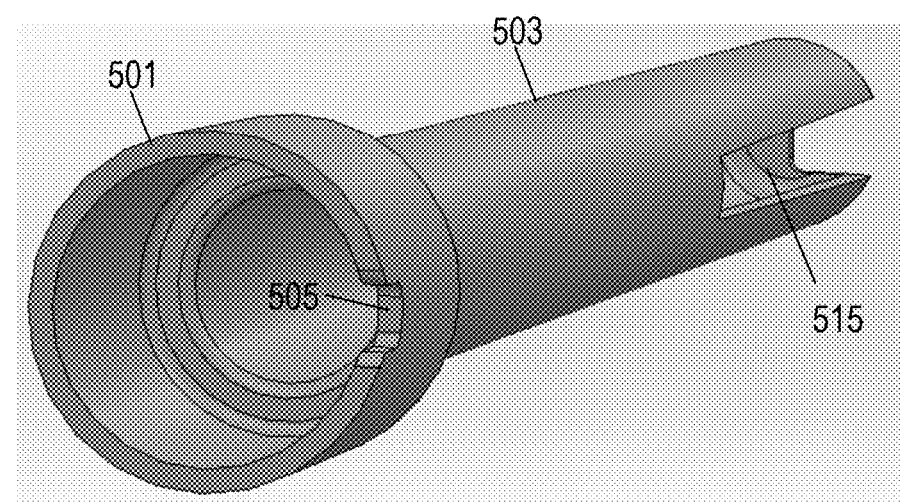
FIG. 5A illustrate an example view of an example suction tube in accordance with one or more embodiments of the present technology.
Figure 5B:
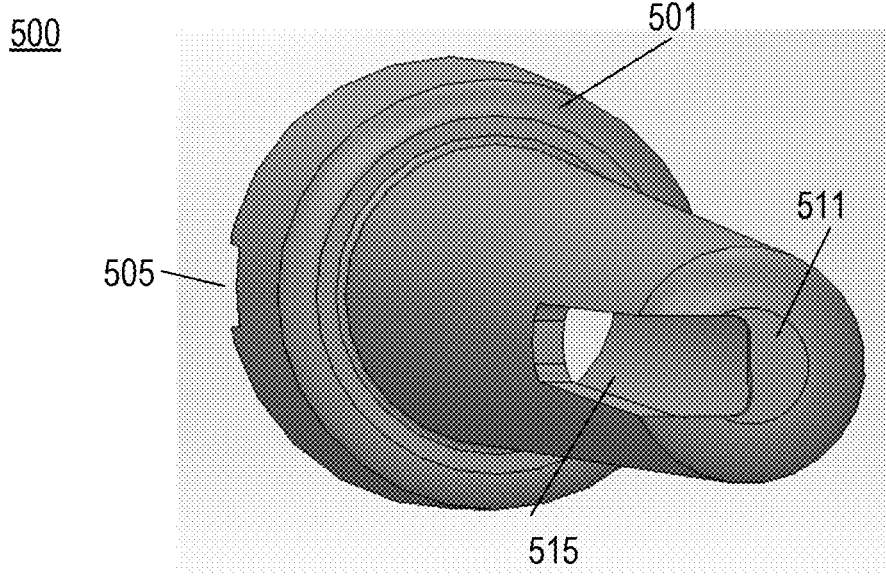
FIG. 5B illustrate another example view of an example suction tube in accordance with one or more embodiments of the present technology.

FIGS. 5A-5B illustrate additional views of an example suction module 500 in accordance with one or more embodiments of the present technology. As shown in FIG. 5A, the suction module 500 includes a base portion 501 that can be removably assembled onto the duct. The base portion 501 includes a notch 505 that corresponds to the ridge of the suction module to enable efficient assembly of the suction module in the correct direction. The suction module also includes a body portion 503. In some embodiments, the body portion 503 can have a shape of a cylinder. In some embodiments, the profile of the body portion 503 has a shape of a trapezoid or can have a rectangular cross-section. As shown in FIG. 5B, the body portion 503 also includes a slit 515. In some embodiments, as shown in FIGS. 5A-5B, the slit can extend to the tip 511 of the body portion to provide optimal airflow control and/or suction efficiency.

Figure 6:
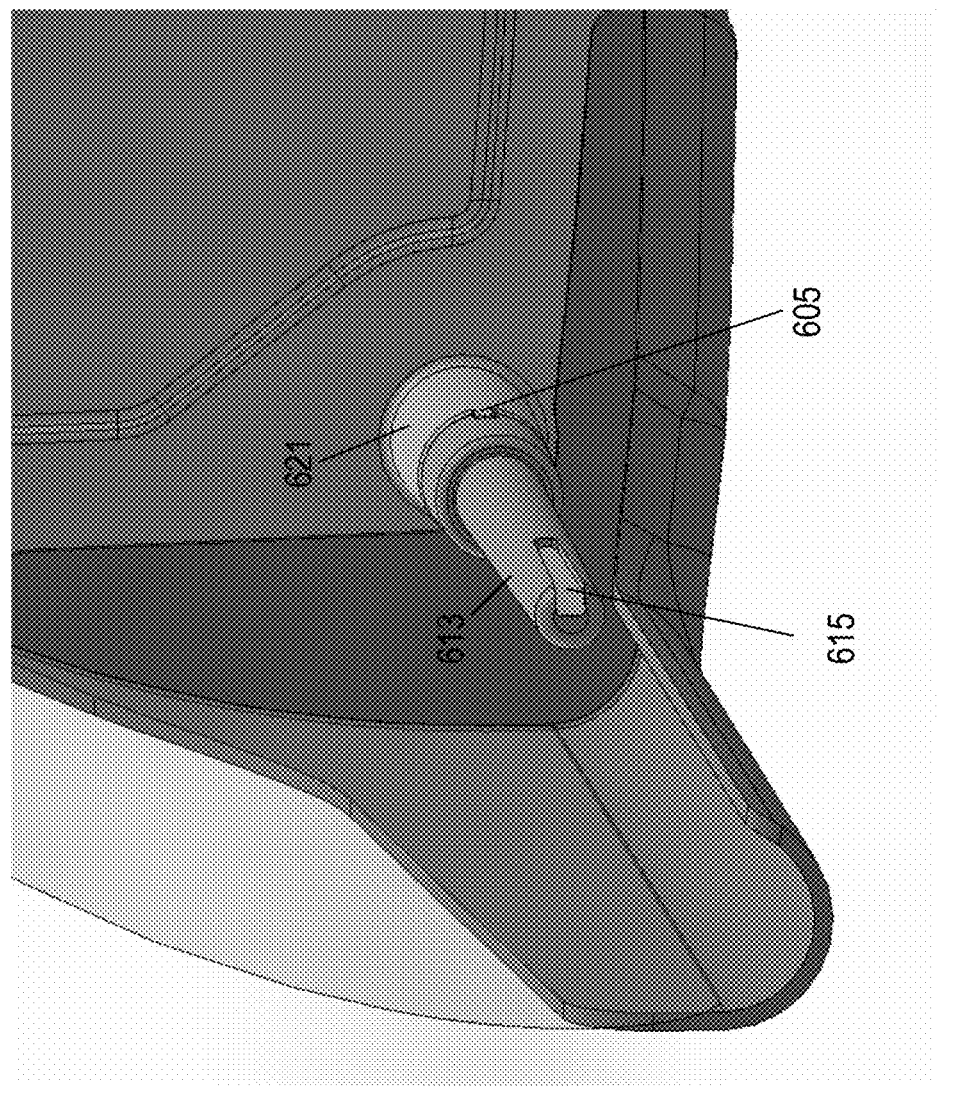
FIG. 6 illustrates an example of a suction tube assembled to a duct portion of a base plate in accordance with one or more embodiments of the present technology.
Figure 7:
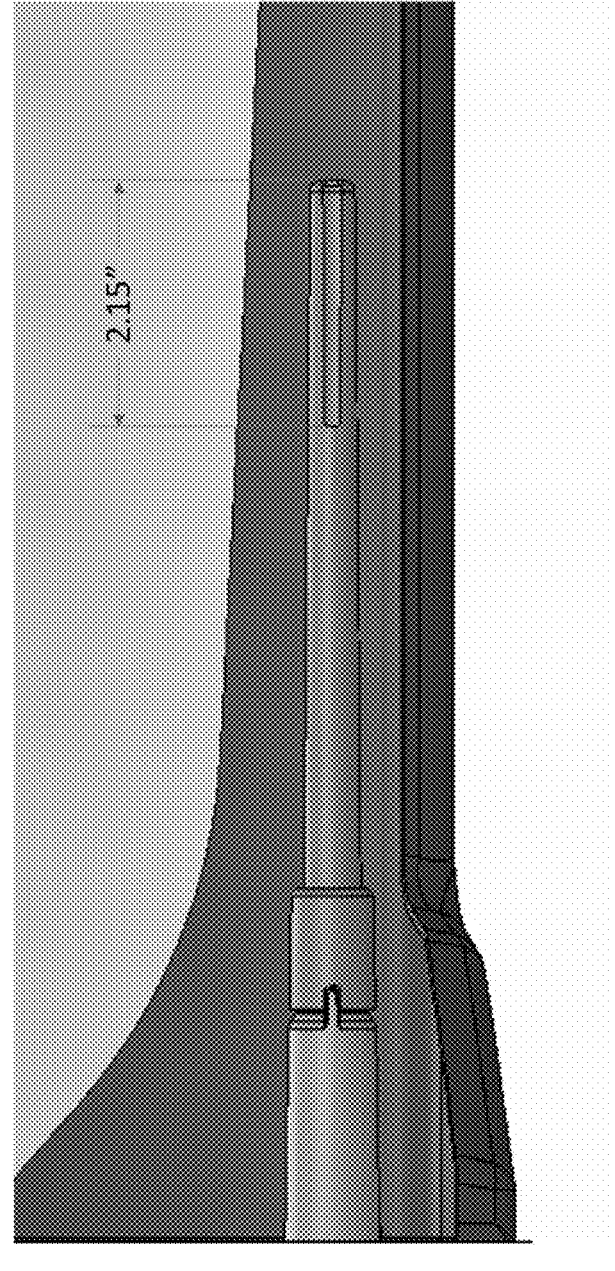
FIG. 7 illustrates another example of a suction tube assembled to a duct portion of a base plate in accordance with one or more embodiments of the present technology.

FIG. 6 illustrates an example of a suction module assembled to a duct portion of a base plate in accordance with one or more embodiments of the present technology. As shown in FIG. 6, the ridge 605 ensures the correct positioning of the suction module 613 such that the slit 615 (extending to the tip of the suction module 613) is positioned horizontally. FIG. 7 illustrates another example of a suction module assembled onto a duct 621 of a base plate in accordance with one or more embodiments of the present technology. Different suction modules having different slit lengths can be provided to allow the healthcare provider to select the most appropriate size for a particular medical or dental procedure. For example, in dental procedures, the length of the slit can be between 1.5 to 3 inches. In some embodiments, the length of the slit is around 2 inches. In the example shown in FIG. 7, the length of the slit is approximately 2.15 inches.

Figure 8A:
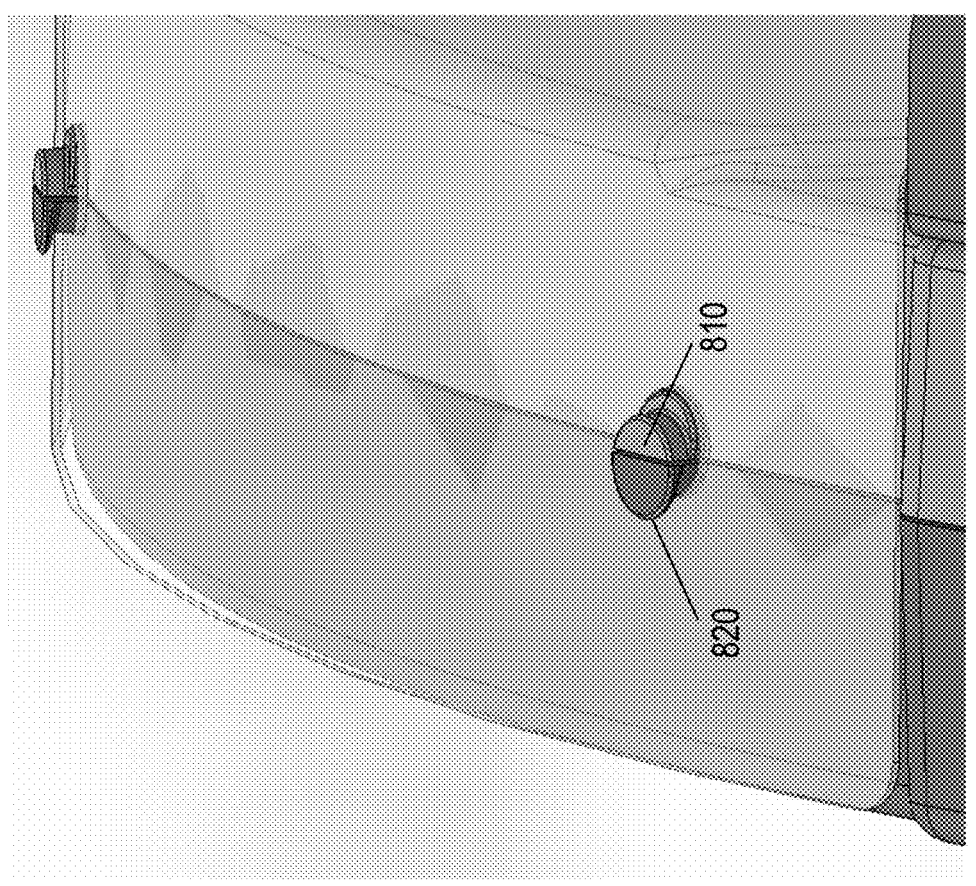
FIG. 8A illustrates an example shield retainer in accordance with one or more embodiments of the present technology.
Figure 8B:
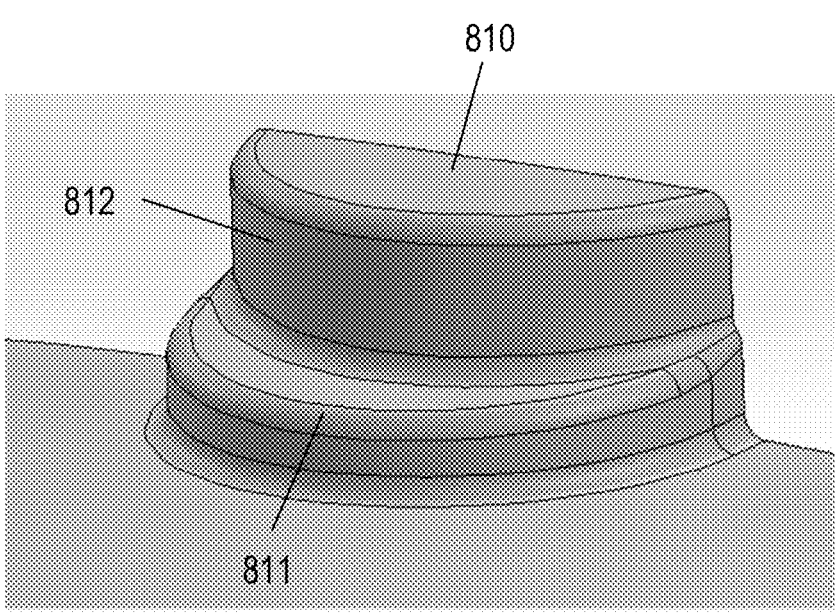
FIG. 8B illustrates one side of an example first section of a shield retainer in accordance with one or more embodiments of the present technology.
Figure 8C:
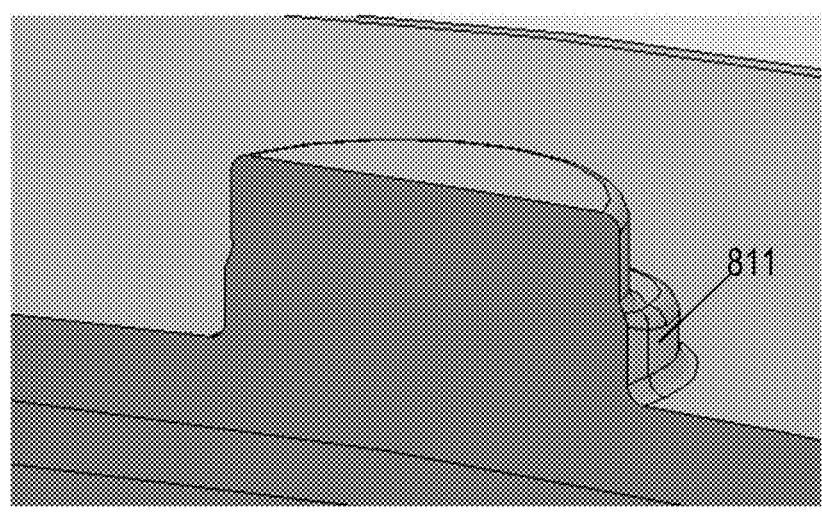
FIG. 8C illustrates another side of an example first section of a shield retainer in accordance with one or more embodiments of the present technology.

As discussed above in connection with FIGS. 2A-B, the first section 211 and the second section 213, when coupled together, form multiple shield retainers 217 that allow the transparent shield 205 to be removably coupled to the base plate 201. FIGS. 8A-8E illustrate example shield retainers in accordance with one or more embodiments of the present technology. In some embodiments, a shield retainer includes two sections: a first section 810 that includes a protrusion extended from the base plate, and a second section 820 that includes a lip portion. FIGS. 8B-8C illustrate two sides of an example first section of a shield retainer in accordance with one or more embodiments of the present technology. As shown in FIG. 8B, one side of the example first section 810 includes a bottom portion 811 that extends or protrudes from the base plate, forming a shoulder-like structure that leads to a top portion 812 having a smaller diameter. In some embodiments, the top portion 812 has a shape of half a cylinder. The other side of the example first section 810 is flushed with the side surface of the base plate to enable a tight fit when the first and second base plate sections are positioned together. In some embodiments, the first section of the shield retainer can be formed as part of the first or the second base plate sections of the base plate.

Figure 8D:
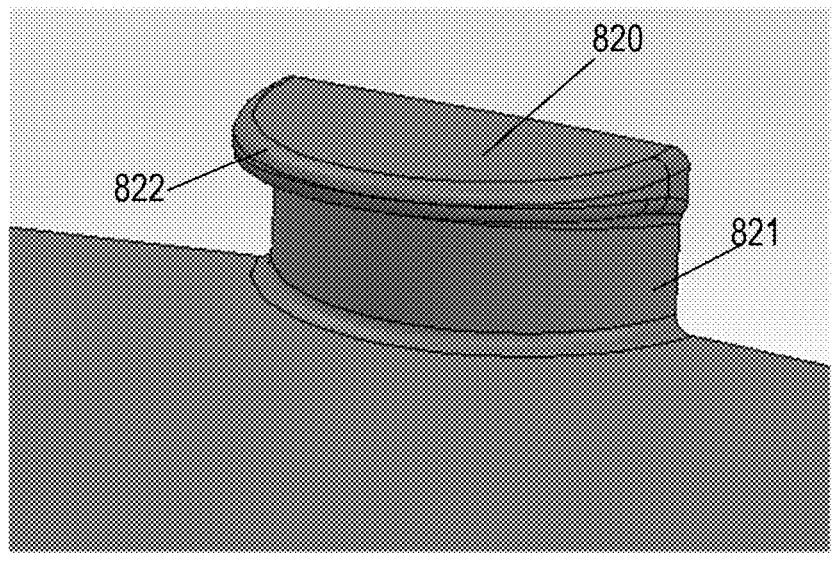
FIG. 8D illustrates one side of an example second section of a shield retainer in accordance with one or more embodiments of the present technology.
Figure 8E:
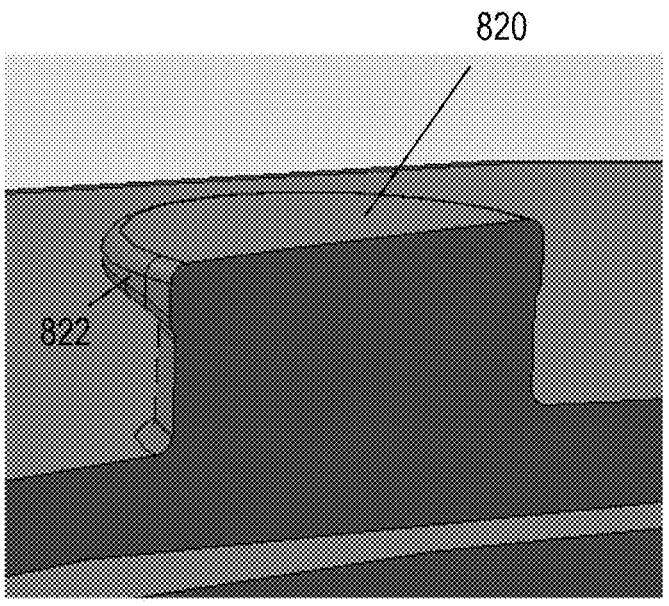
FIG. 8E illustrates another side of an example second section of a shield retainer in accordance with one or more embodiments of the present technology.

FIGS. 8D-8E illustrate two sides of an example second section of a shield retainer in accordance with one or more embodiments of the present technology. As shown in FIG. 8D, one side of the example second section 820 includes a bottom portion 821 and a top portion 822 that extends horizontally to form a lip-shaped overhang. The bottom portion 821 can have a shape of half a cylinder. The other side of the example second section 820, as shown in FIG. 8E, is flushed with the side surface of the base plate to enable a tight fit when the first and second covers are positioned together. In some embodiments, the second section can be formed as part of the second cover or the first cover of the base plate.

Figure 9A:
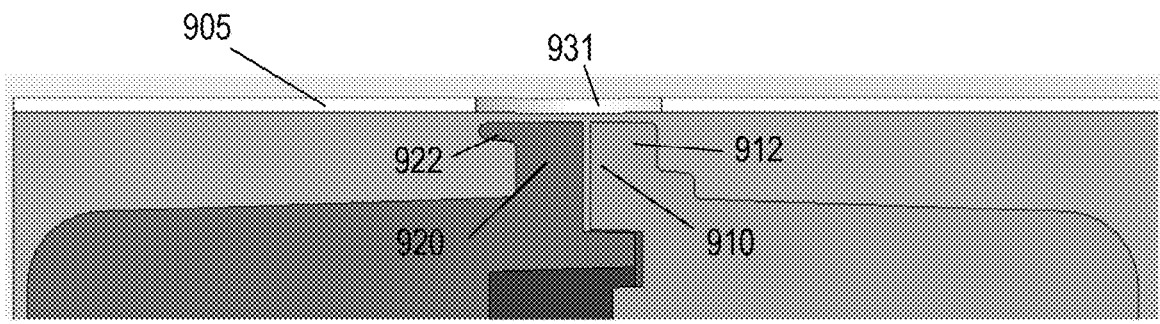
FIG. 9A illustrates an example step of coupling a transparent shield to a base plate using one or more shield retainers in accordance with one or more embodiments of the present technology.
Figure 9B:
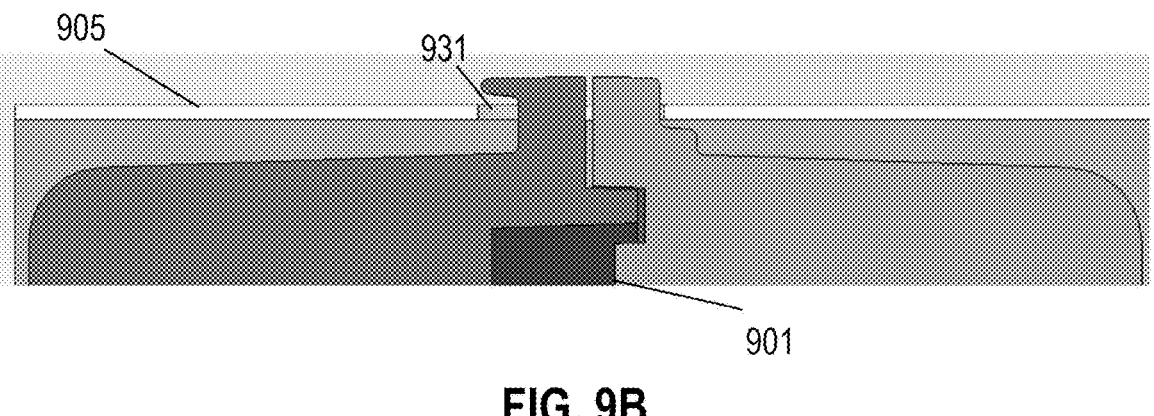
FIG. 9B illustrates another example step of fastening a transparent shield to a base plate using one or more shield retainers in accordance with one or more embodiments of the present technology.
Figure 9C:
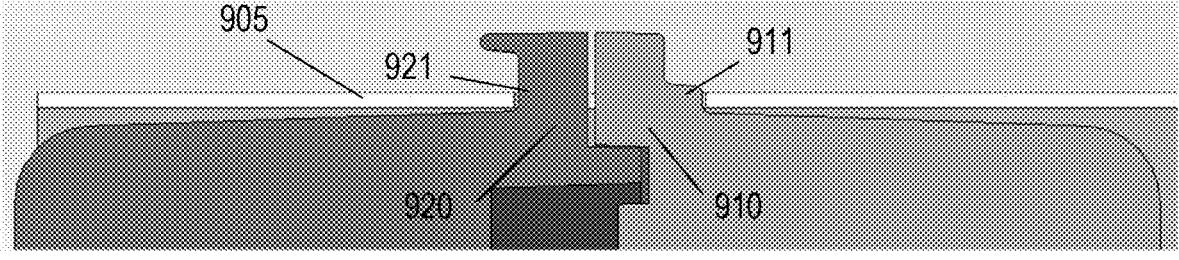
FIG. 9C illustrates yet another example step of fastening a transparent shield to a base plate using one or more shield retainers in accordance with one or more embodiments of the present technology.

FIGS. 9A-9C illustrate an example of coupling a transparent shield to a base plate using one or more shield retainers in accordance with one or more embodiments of the present technology. As shown in FIG. 9A, the transparent shield 905 includes one or more holes 931. The size of each of the one or more holes 931 is approximability the same as the size of the top part of the shield retainer, which is formed by the lip-shaped overhang 922 of the second section 920 and the top portion 912 of the first section 910. The top part of the shield retainer can go through the hole 931 of the transparent shield 905 such that the transparent shield 905 can be positioned towards the base plate 901, as shown in FIG. 9B. The transparent shield 905 can further be slid sideways towards the bottom portion 911 of the first section 910 so that the hole 931 is snugly fit with the bottom part of the shield retainer formed by the bottom portion 911 of the first section 910 and the bottom portion 921 of the second section 920.

The shape of the protrusion and the overhang of the shield retainers provides a two-stage process for installation, thereby ensuring secure attachment of the transparent shield. In some embodiments, the base plate includes three to five shield retainers. In some embodiments, more shield retainers can be provided on the base plate to ensure secure coupling of the transparent shield. Because the shield retainers are formed as part of the base plate, the manufacturing process is simplified with lower costs.

Figure 10A:
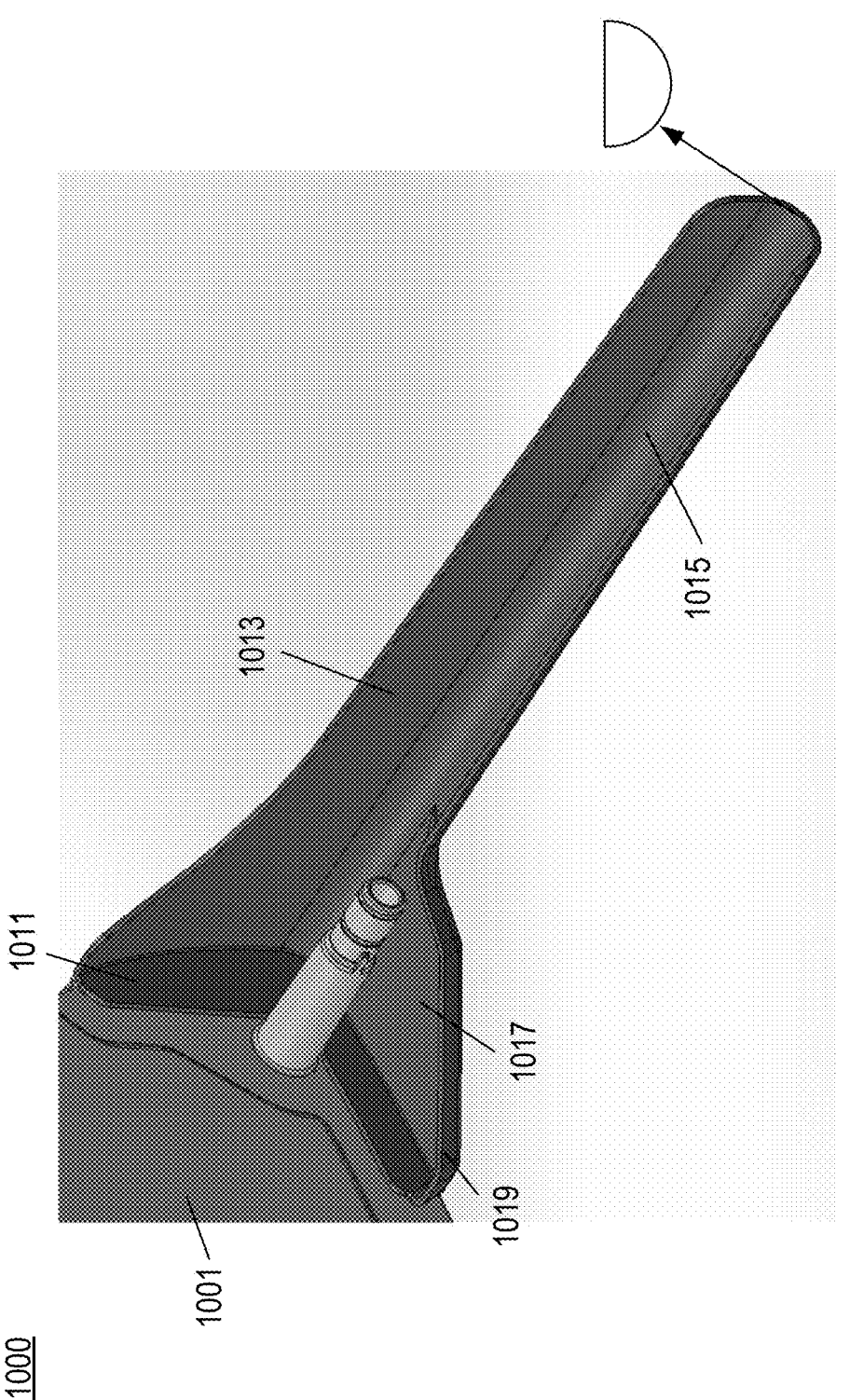
FIG. 10A illustrates an example fluid drip pan connected to a base plate in accordance with one or more embodiments of the present technology.
Figure 10B:
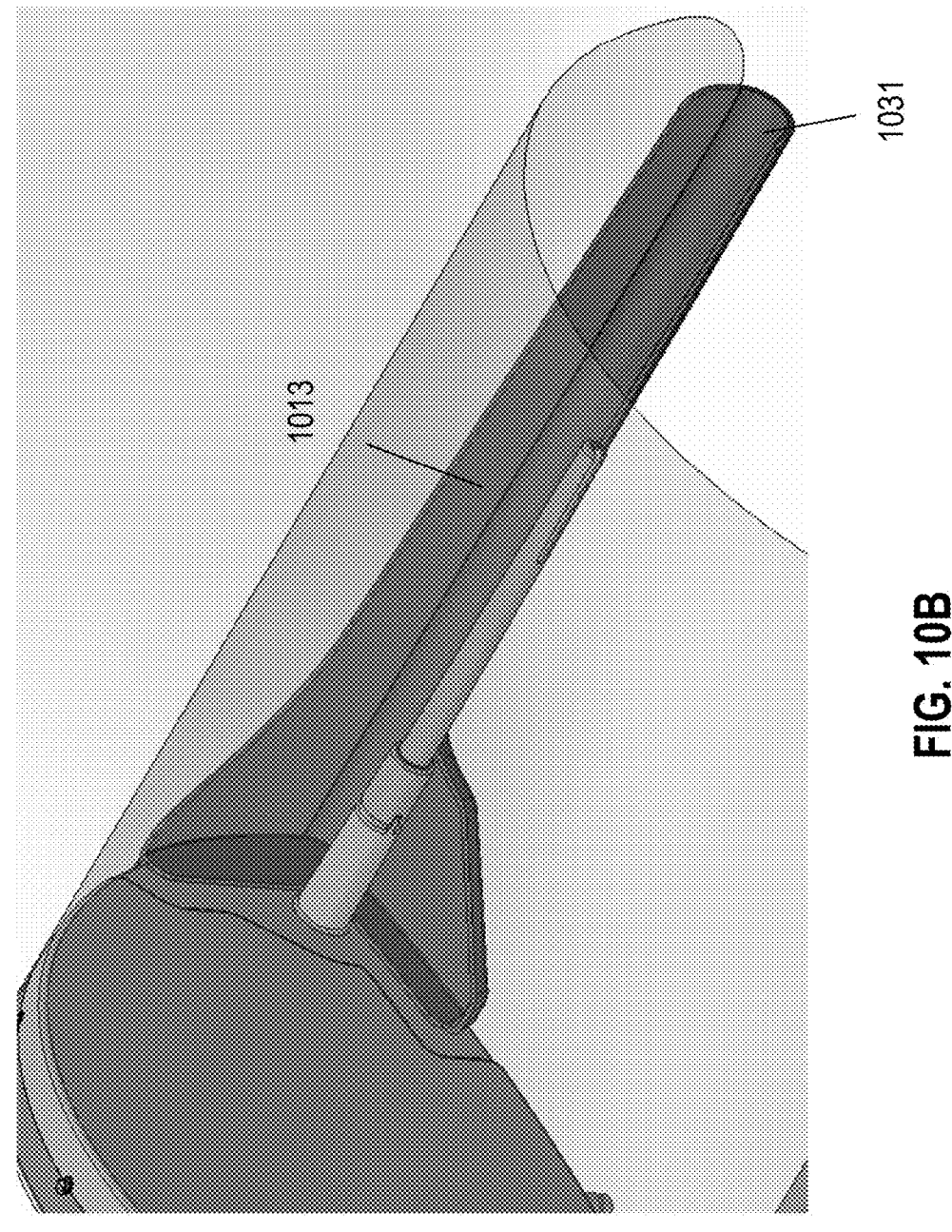
FIG. 10B illustrates the example fluid drip pan shown in FIG. 10A with a transparent shield and a suction tube assembled in accordance with one or more embodiments of the present technology.

Referring back to FIG. 2A, the shield protection system also includes two fluid (or moisture) collection troughs 207*a*, 207*b* to catch the fluid that forms on and drips from the transparent shield 205. FIG. 10A illustrates an example fluid collection trough 1000 connected to a base plate in accordance with one or more embodiments of the present technology. The fluid collection trough 1000 includes a base section 1011 that can be shaped to, for example, follow a contour of the base plate 1001. The fluid collection trough 1000 includes a vertical curved section 1013 that can function as a stopper to maintain the curved shape of the transparent shield once it is installed. The fluid collection trough 1000 includes a curved channel 1015 that can function as a fluid/moisture catch to collect the fluid that is formed on the patient-facing side of the transparent shield and ultimately moves to the sides of the transparent shield and onto the troughs at least in-part due to the airflow circulation caused by the suction pump. In some embodiments, the curved channel 1015 can form an arc that is around 180 degrees, as shown in the semi-circular illustration at the tip of the trough in FIG. 10A. In some embodiments, collection troughs with larger than 180 degrees can be implemented to reduce the risk of fluid leaks from the curved channel. The fluid drip pan also includes a pan section 1017 that is connected to the curved channel 1015 to collect the fluid that flows into the channel. The pan section 1017 includes a bottom surface and a barrier 1019. The bottom surface can be slightly tilted to facilitate the movement of the fluid into the pan section 1017. The barrier 1019 is connected with the base section 1011 and the curved channel 1015 to prevent the collected liquid from spilling to the patient. FIG. 10B illustrates the example fluid collection trough 1000 with a transparent shield and a suction tube assembled in accordance with one or more embodiments of the present technology. As shown in FIG. 10B, the vertical curved section 1013 pushes against the transparent shield when it is installed to maintain the curved shape of the transparent shield. In some embodiments, the fluid collection trough comprises a solid material (e.g., hard plastic) and can function as a handle for the protective shield system in addition to its function to collect fluid from the transparent shield. A healthcare provider can hold on to the tip or side of the collection trough 1031 and adjust the position and/or orientation of the protection shield system with respect to the patient.

Figure 11:
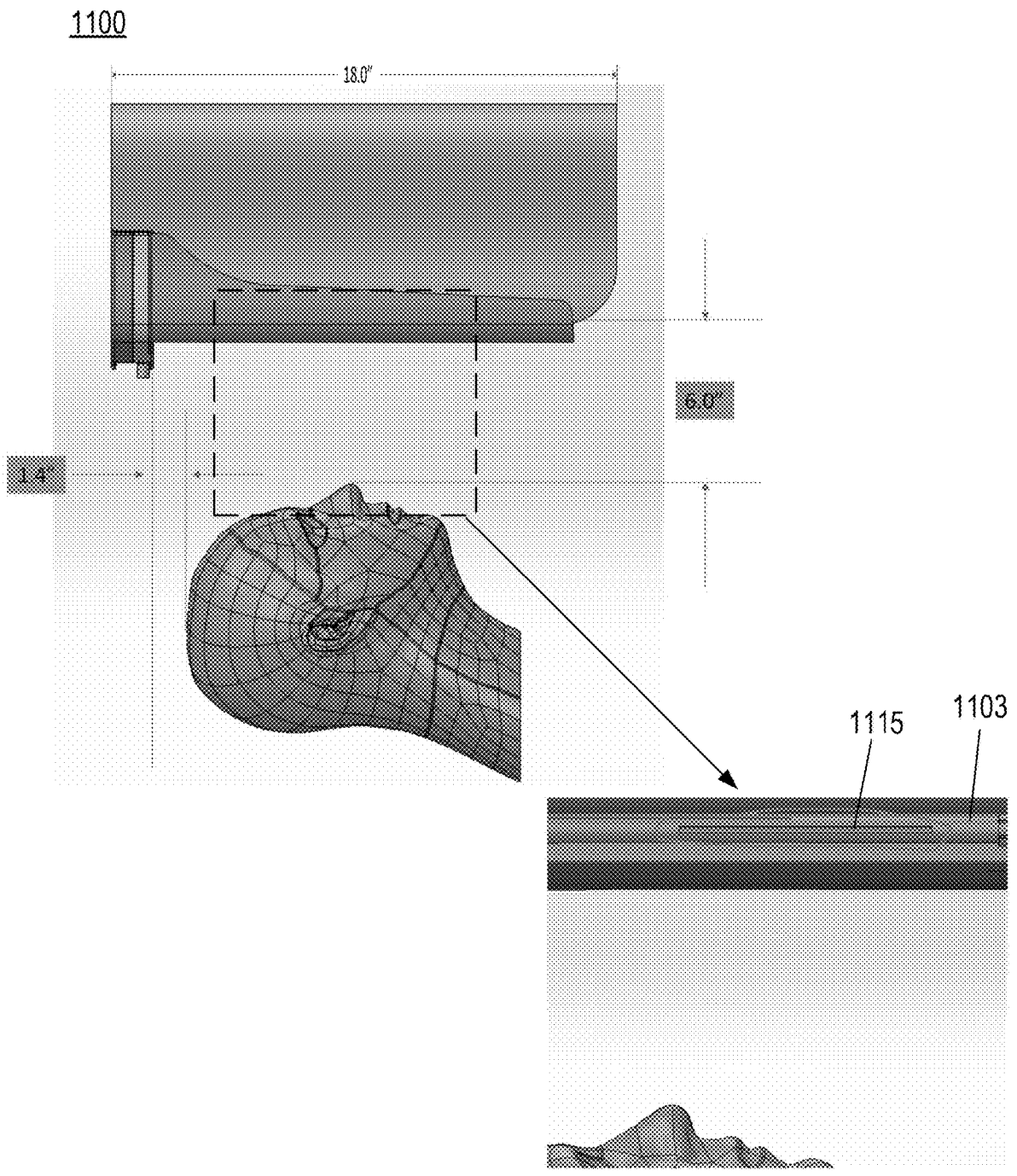
FIG. 11 illustrates an example configuration of a protective shield system with respect to a patient in accordance with one or more embodiments of the present technology.

FIG. 11 illustrates an example configuration 1100 of a protective shield system with respect to a patient in accordance with one or more embodiments of the present technology. During the procedure, the protective shield system can be positioned above the patient, with the base plate extending beyond patient's head. For example, in dental procedures, as shown in the lower right section of FIG. 11, the suction module 1103 can be positioned to be aligned with and be on top of the nose and mouth of the patient, with the slit 1115 facing inwards to achieve optimal airflow control, suction and collection of the aerosol droplets or particulates. It should be noted that the positioning of the slit in the horizontal orientation, the dimensions of the troughs and other dimensions and positions can be adjusted to produce a desired collection and removal behavior of the shield system, as well as a target cost for manufacturing and assembly of the parts. For example, airflow studies conducted by the inventors have revealed that having a single slit (for each suction module) that is positioned in a horizontal position produces a desired configuration that results in good airflow, fluid collection and fluid/particulate removal. In the example shown in FIG. 11, the protective shield system is placed approximately six inches above the patient's head and extends approximately 1.4 inches beyond the patient's head. In some embodiments, the length of the transparent shield is between 15 to 20 inches. Different lengths and/or different positions of the protective shield system can be provided to accommodate different patients and/or different types of procedures.

Figure 12:
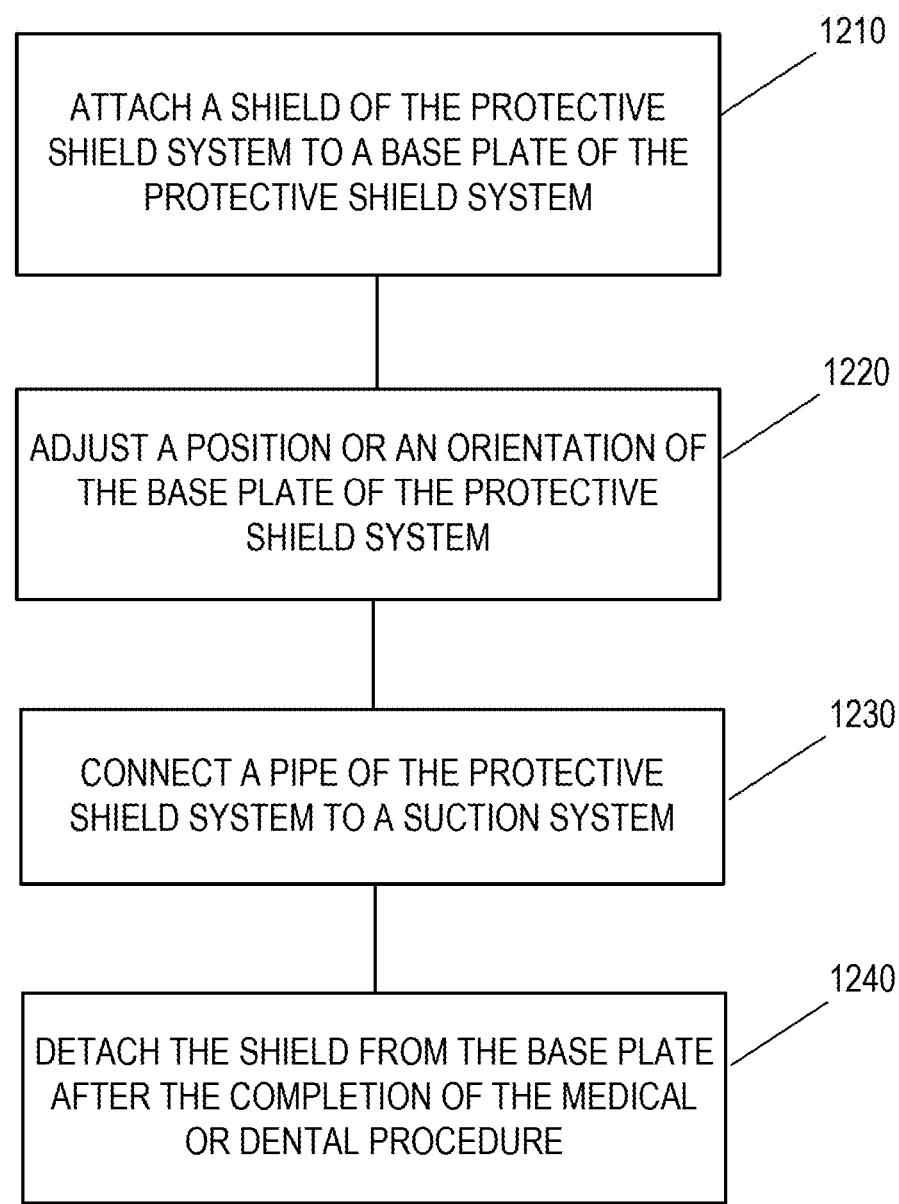
FIG. 12 is a flowchart representation of a method for performing a medical or dental procedure in accordance with one or more embodiments of the present technology.

FIG. 12 is a flowchart representation of a method for performing a medical or dental procedure in accordance with one or more embodiments of the present technology. The method 1200 includes, at operation 1210, attaching a transparent shield of the protective shield system to a base plate of the protective shield system via one or more shield retainers. The method 1200 includes, at operation 1220, adjusting a position or an orientation of a base plate of a protective shield system based on manipulating a handle of the base plate. A first end of the support arm is connected to the base plate and a second end of the support arm is fixated on an operating platform. The method 1200 includes, at operation 1230, connecting a pipe of the protective shield system to a suction system. The pipe interface is formed by a first cover and a second cover of the base plate. The pipe can be configured to remove, via the suction system, aerosol droplets or condensation of the aerosol droplets on the transparent shield generated during the medical or the dental procedure through two suction tubes that are removably coupled to two ducts of the base plate. The method 1200 also includes, at operation 1240, performing the medical or dental procedure on a patient while the suction system operates.

In some embodiments, the method includes positioning the transparent shield to allow the top portion of the second section of each shield container to go through a corresponding hole, and sliding the transparent shield towards the bottom portion of the first section of each shield container to enable a snug fit between the one or more holes of the transparent shield and the one or more shield retainers. In some embodiments, the method includes replacing or sanitizing the transparent shield after the medical or dental procedure. In some embodiments, the method includes replacing or sanitizing the two suction tubes after the medical or dental procedure. In some embodiments, the suction system is a portable suction system and the method further includes relocating the protective shield system with the portable suction system after the medical or dental procedure.

In one example aspect, a protective shield system for a medical or dental procedure includes a base plate that is flat and has a curved edge. The base plate includes a first cover and a second cover. The first cover and the second cover are configured to form at least part of a pipe system when coupled together, the pipe system having two ducts and an interface configured to be connected to a vacuum suction system. The first cover and the second cover are further configured to form one or more shield retainers when coupled together. The protective shield system also includes two suction tubes that are removably coupled to the two ducts of the pipe system and a shield having at least one transparent section. The shield is configured to be removably coupled to the base plate via the one or more shield retainers and one or more holes on the shield so as to allow attachment of the shield to the base plate prior to the medical or dental procedure and removal of the shield from the base plate after the medical or dental procedure. When in an attached configuration, the shield forms a curved surface that includes the at least one transparent section and forms a space bounded by the curved surface configured to allow access to a patient for performing the medical or dental procedure.

In some embodiments, the first cover of the base plate comprises a channel that connects the two ducts and the interface. In some embodiments, the first cover of the base plate further comprises a sealing component configured to seal the channel. In some embodiments, each of the one or more shield retainers is formed by a first section on the first cover and a second section on the second cover, wherein the first section comprises a bottom portion that protrudes from the base plate, and wherein the second section comprises a top portion that extends horizontally to form an overhang.

In some embodiments, each of the two suction tubes comprises a slit that extends to a tip of the suction tube. In some embodiments, each of the two ducts comprises a ridge, and each of the two suction tubes comprises a notch. The notch corresponds to the ridge such that a suction tube is assembled to a corresponding duct in a direction such that the slit is faced toward the patient.

In some embodiments, the base plate comprises a handle. In some embodiments, the protective shield system is configured to be attached to a ceiling of an operating room via an adjustable arm. In some embodiments, the protective shield system is configured to be attached to a portable system that comprises the vacuum suction system. In some embodiments, the system further includes two fluid drip pans coupled to the base plate configured to collect fluid formed on the shield.

It will be appreciated that the disclosed protective shield system can provide a higher level of protection for healthcare personnel against communicable diseases. The transparent shield allows a healthcare professional to clearly view the operating area during a medical or dental procedure while preventing aerosol droplets or mists from splashing onto the healthcare professional. The base plate that the transparent shield is attached to can be flexibly controlled before or during the procedure to ensure that there is sufficient room underneath the transparent shield to operate on the patient. Furthermore, the vacuum pipe in contact with the transparent shield is connected to a vacuum suction system to remove any condensation of the droplets or mists on the transparent shield, thereby eliminating the possibility of the condensation dripping onto unprotected surfaces.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A protective shield system for a medical or dental procedure, comprising:
a base plate that is flat and has a curved edge, wherein the base plate comprises a first cover and a second cover, wherein the first cover and the second cover are configured to form at least part of a pipe system when coupled together, the pipe system comprising two ducts and an interface configured to be connected to a vacuum suction system, and wherein the first cover and the second cover are further configured to form one or more shield retainers when coupled together;
two suction tubes that are removably coupled to the two ducts of the pipe system; and
a shield having at least one transparent section, the shield configured to be removably coupled to the base plate via the one or more shield retainers and one or more holes on the shield so as to allow attachment of the shield to the base plate prior to the medical or dental procedure and removal of the shield from the base plate after the medical or dental procedure, wherein, when in an attached configuration, the shield forms a curved surface that includes the at least one transparent section and forms a space bounded by the curved surface configured to allow access to a patient for performing the medical or dental procedure.

2. The protective shield system of claim 1, wherein the first cover of the base plate comprises a channel that connects the two ducts and the interface.

3. The protective shield system of claim 2, wherein the first cover of the base plate further comprises a seal configured to seal the channel.

4. The protective shield system of claim 1, wherein each of the one or more shield retainers is formed by a first section on the first cover and a second section on the second cover, wherein the first section comprises a bottom portion that protrudes from the base plate, and wherein the second section comprises a top portion that extends horizontally to form an overhang.

5. The protective shield system of claim 1, each of the two suction tubes comprises a slit that extends to a tip of the respective suction tube.

6. The protective shield system of claim 5, wherein each of the two ducts comprises a ridge, and each of the two suction tubes comprises a notch, wherein each notch corresponds to a respective ridge such that each suction tube is assembled to a corresponding duct in a direction such that each slit is configured to be faced toward the patient in use.

7. The protective shield system of claim 1, wherein the base plate comprises a handle.

8. The protective shield system of claim 1, wherein the protective shield system is configured to be attached to a ceiling of an operating room via an adjustable arm.

9. The protective shield system of claim 1, wherein the protective shield system is configured to be attached to a portable system that comprises the vacuum suction system.

10. The protective shield system of claim 1, further comprising:

two fluid drip pans coupled to the base plate configured to collect fluid formed on the shield.

* * * * *